(12) United States Patent
Schönenberger et al.

(10) Patent No.: US 6,860,852 B2
(45) Date of Patent: Mar. 1, 2005

(54) ULTRASOUND THERAPEUTIC DEVICE

(75) Inventors: Klaus Schönenberger, Ecublens (CH);
Félix Buhlmann, Lausanne (CH);
Pierre-Yves Muller, Collonge-Bellerive (CH); Pierre Rigaux, Verlaine (BE)

(73) Assignee: Compex Medical S.A., Ecublens (CH)

( * ) Notice: Subject to any disclaimer, the term of this patent is extended or adjusted under 35 U.S.C. 154(b) by 239 days.

(21) Appl. No.: 10/281,090

(22) Filed: Oct. 25, 2002

(65) Prior Publication Data

US 2004/0082857 A1 Apr. 29, 2004

(51) Int. Cl.[7] ................................................. A61B 8/00
(52) U.S. Cl. .................................................... 600/439
(58) Field of Search .............................. 600/407–472; 601/2, 3; 73/625, 626; 367/7, 11, 130, 138

(56) References Cited

U.S. PATENT DOCUMENTS

| | | | |
|---|---|---|---|
| 4,368,410 A | 1/1983 | Hance et al. | 318/116 |
| 4,614,178 A | 9/1986 | Harlt et al. | 128/24 |
| 4,791,915 A | 12/1988 | Barsotti et al. | 128/24 |
| 4,823,775 A | 4/1989 | Rindt | 128/24 |
| 4,938,217 A | 7/1990 | Lele | 128/399 |
| 4,966,131 A | 10/1990 | Houghton et al. | 128/24 |
| 5,016,615 A | 5/1991 | Driller et al. | 128/24 |
| 5,095,890 A | 3/1992 | Houghton et al. | 128/24 |
| 5,184,605 A | 2/1993 | Grzeszykowski | 128/24 |
| 5,267,985 A | 12/1993 | Shimada et al. | 604/290 |
| 5,323,769 A | 6/1994 | Bommannan et al. | 601/2 |
| 5,413,550 A | 5/1995 | Castel | 601/2 |
| 5,460,595 A | 10/1995 | Hall et al. | 601/2 |
| 5,601,526 A | 2/1997 | Chapelon et al. | 601/3 |
| 6,113,559 A | 9/2000 | Klopotek | 601/3 |

OTHER PUBLICATIONS

Kerry G. Baker et al., *A Review of Therapeutic Ultrasound: Biophysical Effects, Physical Therapy*, Jul. 2001, vol. 81, pp. 1351–1358.

Betty Tabakovic Oakley, *Penetrating the Problem, Rehab Management International*, Apr./May 2000, pp. 1–3.

R.C. Greenwald et al., *A Computer Controlled System for Ultrasonic Hyperthermia Treatment, Eight Annual Northeast Bioengineering Conference*, Mar. 1980, 6 pp.

*Primary Examiner*—Ali Imam
(74) *Attorney, Agent, or Firm*—Patterson, Thuente, Skaar & Christensen, P.A.

(57) ABSTRACT

The ultrasound therapeutic system of the present invention generally includes a generator unit, at least one transducer treatment head, and a programmable controller. The generator is in operable communication with the at least one transducer treatment head such that electric power outputted from the generator to the head is converted into acoustic power by the head. Re-programmable software at the controller generally controls all features and functions for the system. In particular, the controller calculates an initial optimal treatment dose, maintains effective acoustic power transmitted to the patient through the at least one treatment head, performs calibration procedures for the at least one treatment head, controls outputting for each supported treatment mode, and provides for various other features and functions.

37 Claims, 6 Drawing Sheets

ULTRASOUND THERAPEUTIC DEVICE

FIELD OF THE INVENTION

The present invention generally relates to the field of ultrasound treatment. More specifically, the present invention relates to an ultrasound therapeutic device capable of automatically determining a considerate treatment dose, controlling acoustic power output efficiency, and performing adjustable calibration functions.

BACKGROUND OF THE INVENTION

Therapeutic ultrasound devices have long been utilized in the treatment of musculoskeletal and tissue injuries. Greater understanding of ultrasound, and the application of ultrasound to human skin and tissue, have expanded the scope of possible uses for these devices. For instance, in addition to the thermal or vibratory focus of more traditional devices, developments have been made in which ultrasound devices can be directed toward introducing various drugs into the human body through the skin. However, the increase in potential uses and advantages for these therapeutic ultrasound devices has come at a price. Namely, advancements in the technology and the understanding of the potential applications, has correspondingly led to the complication of setup procedures, inefficient power adjustments, and the need for more precise calibration procedures.

Initial Parameter Inputs

Ultrasonic therapy devices impose mechanical vibrations on tissue and skin to cause various thermal and non-thermal effects. An ultrasound generator outputs electric power to a treatment head. The treatment head includes a transducer which converts the power from the generator into ultrasonic energy or acoustic power. It is this acoustic power that is transmitted for therapeutic treatment through the patient's tissue. The requisite acoustic power can vary greatly depending on the treatment goals, the target tissue type, the target tissue depth, and other like factors. In addition, the duration of the ultrasonic treatment dosage to the patient is important. Treatment goals, the unique characteristics of the target tissue, and like considerations dictate the treatment duration.

Conventional ultrasound treatment devices generate a treatment dose based on manually inputted values or parameters. Parameters such as treatment time/duration, frequency, and treatment intensity are inputted by the end user. Generally, with such devices, calculations and determinations are made by the user. Consequently, it is up to the device user to come up with the ideal treatment parameters required for a specific patient, assuming specific treatment goals for that patient.

There are many drawbacks with manually operated devices. Specifically, it is problematic that these manual systems are reliant upon the skills and knowledge of the individual user. This problem manifests itself in at least two respects. First, there is no way to know or control exactly what factors are being considered by the user in calculating the proper treatment parameters. For example, there are no guarantees that the end user will properly consider the target tissue characteristics, the target tissue type, or the existence and depth of any intermediate tissue between the treatment head and the target tissue. These are all highly relevant factors that should play a primary role in determining the proper treatment outputs and durations for any effective ultrasound therapeutic treatment. In addition, accidental parameter entries, and the varying level of user training introduce still more uncertainty into the likelihood of providing optimized ultrasound treatment for the patient.

As indicated, the unique and specific characteristics of the target tissue, and the nature and thickness of intermediate tissue and/or the target tissue, are requisite factors to be considered in determining a proper ultrasound treatment dose. This is true since both the thermal and non-thermal effects of ultrasound are dependent upon these factors. Despite the fundamental importance of these considerations, conventional ultrasound therapeutic devices simply have not advanced methods and apparatus that properly consider and process known histological tissue characteristics in generating a treatment dose.

U.S. Pat. No. 5,413,550 ("the '550 Patent") discloses an attempt to provide for considerate dose control. The '550 Patent is directed to an ultrasound device including a controller programmed to calculate a treatment dose. The treatment dose consists of treatment frequency, output intensity, and treatment time. The programmed controller determines and generates the dosage parameters based on the inputting of numerous treatment parameters by the end user. Specifically, the device requires values for the following primary treatment parameters in order to calculate a dosage: depth of tissue to be treated, the desired tissue temperature rise, the tissue area to be treated, and the selection of an ultrasound couplant. In addition the user may input the tissue type, and a duty factor value as secondary parameters.

The device of the '550 patent performs routine checks to determine if treatment parameters have been entered. If the controller determines that specific primary treatment parameters have not been inputted, the controller circuitry inserts a default value in place of the missing parameter(s). As a result, it is possible to enter only one of the primary treatment parameters, with each of the remaining parameters being substituted for default values. Such a default-driven device and process is problematic and fails to properly focus the ultrasound treatment on ultrasound effects and histological tissue data.

The use of default parameters to calculate dosage, by definition, fails to take into account the unique circumstances and characteristics of the patient, the treatment goals for the specific target tissue of the patient, and like goals and considerations that are essential in providing highly efficient and effective ultrasound treatment. As indicated herein, knowledge and specific consideration of the unique target treatment tissue, and the depth of that tissue or the thickness of intermediate tissue, are essential in generating an optimal treatment dose. Generating a dose, regardless of the automated nature of the calculation, is deficient if it fails to account for the true tissue structure, such as the energy losses produced as a result of tissue heating, and the losses caused by adjacent tissue structure. Ignoring such essential characteristics of treatment on complex tissue structures dilutes the efficacy of the dosage calculation. Proper acoustic power outputs and treatment durations must be specified, monitored, and updated in a manner most beneficial for the treatment goals for the unique individual patient, after fully understanding and processing data pertaining to the target tissue, intermediate tissue, and tissue depths.

Treatment Dose Adjustments

Conventional ultrasonic therapeutic devices and systems are generally deficient when it comes to the continuous and efficient monitoring and controlling of the power being outputted from the generator to the transducer. The typical approach to controlling, acoustic power from the transducer head is to merely provide alarm and display notices to the user. For example, U.S. Pat. No. 4,791,915 is directed to a device wherein the coupling efficiency between the transducer and the patient is displayed in the form of a readable bar graph for the user to observe and monitor. However, such systems and devices merely focus on preventing overheating and electrical shorting. Threshold comparisons are merely made in order to prevent catastrophic failures which could cause device malfunction and/or injury to the patient.

Other conventional ultrasound treatment systems implement adjustment techniques and controls directed to providing for a relatively constant electric power output level to the patient. For instance, U.S. Pat. No. 4,368,410 discloses an ultrasound therapy device wherein an optimal electric output power level is inputted into the device. Feedback signals from a driver circuit proportional to the transducer voltage and current are returned to an analog servo circuit and a voltage representing true electric power is calculated. If the output power represented by the voltage level increases then it is an indication that there is a reduction in the load on the transducer, and the drive signal is decreased. Similarly, if the instant voltage decreases, an increase in the signal is initiated to compensate for an increase in the load on the transducer. The innate problem with such a system is that while it does acknowledge the effects varying treatment techniques, treatment zones, and an individuals body can have on ultrasound treatment, it does not properly use this information in providing for a truly responsive individualized treatment dosage. Focus is on maintaining a constant electric power output and not on performing acoustic analysis. Events and circumstances effecting the ultrasound treatment are not properly considered—i.e., the introduction of intermediate tissue, the natural changes across a patient's body "zones", and the like.

Treatment Head Calibration

Each treatment head of an ultrasound therapeutic device requires calibration. Primarily, this calibration is needed in order to accommodate and adjust for, various innate properties and characteristics unique to particular heads. The head must be properly calibrated in order to correctly match the specific resonance frequencies of its constituent ceramic. For instance, each ceramic treatment head varies in its material properties. As a result, proper operation and acoustic output for each and every head mandates at least an initial head calibration. Typically, this calibration is done in the factory prior to receipt of the device by the end user. In many cases, this is the only calibration allowed for, and any later re-calibration must again occur at the factory. However, these factory calibrations are problematic since untimely degeneration can adversely affect treatment quality and effectiveness.

Even those conventional devices that permit for user-initiated calibration require the initiation of complicated or time-consuming procedures. Specifically, it is common to allow for user calibration by immersing the head in water and making a series of adjustments based on calibration readings displayed by the device. For obvious reasons, such techniques are undesirable and inconvenient. Additionally, conventional devices do not consider complex changes introduced by slight imaginary components in the acoustic impedance of the tissues being treated. Conventional devices are thus unable to transmit an accurate amount of power to the tissue or fully self-calibrate.

As a result, there is a need for an ultrasonic therapeutic device, and method for operating and controlling thereof, that substantially solves the problems and deficiencies described in the prior art.

SUMMARY OF THE INVENTION

The ultrasound therapeutic system and methods in accordance with the present invention substantially solve the problems and weaknesses present in the prior art devices and methods. The present invention is generally directed to an ultrasound treatment system wherein it is preferred that each of the described prior art deficiencies are addressed in one device. In general, the ultrasound device and methods of the present invention are directed to providing an optimal initial treatment dose based on complete processing of user-inputted histological tissue data, employing an automatic regulatory feedback loop to maintain optimal acoustic power output to the patient during operation, and providing a simple yet efficient user-initiated treatment head calibration technique. Further, the treatment system of the present invention includes multi-mode treatment techniques/effects, and user-specific memorization functions.

The ultrasound therapeutic system of the present invention generally includes a generator unit, at least one transducer treatment head, and a programmable controller. The generator is in operable communication with the at least one transducer treatment head such that electric power outputted from the generator to the head is converted into acoustic power by the head. Re-programmable software at the controller generally controls all features and functions for the system. In particular, the controller calculates an initial optimal treatment dose, maintains effective acoustic power transmitted to the patient through the at least one treatment head, performs calibration procedures for the at least one treatment head, controls outputting for each supported treatment mode, and provides for various other features and functions as will be discussed in further detail herein.

Unlike the prior art, the present invention is directed to intelligent and simplified automatic dosage determination. Specifically, the output dose is calculated by processing values inputted by the user for target tissue type, intermediate tissue type, and tissue depth/thickness. The present invention does not import or process arbitrary default values for treatment couplant, tissue configuration, and the like. Instead, dosage is based on the fundamental tissue data inputted, wherein the controller performs simulation comparisons to derive the smallest dosage needed to optimally achieve the therapeutic treatment effect. Further, the dosage determination of the present invention, through processing of the inputted histological tissue data, takes into account the relevant tissue layer structure to adjust for the effects caused by innate losses through tissue absorption and reflections caused by impedance discontinuities between different tissue layers. Wave reflection and absorption characteristics are dynamically considered in order to properly understand the resulting output that will be delivered to the target tissue of the patient in light of the relevant tissue structure.

The feedback loop of the present invention is also considerate in its function. Rather than seeking to maintain a constant electrical output, as is often practiced in conventional devices, the ultrasound device of the present invention controls and monitors the effects of the treatment on the transducer head to maintain a constant ideal acoustic power. As a result, changes that may occur naturally during treatment, such as changes caused by the innate acoustic properties-of the tissues proximate the treatment head, are properly considered.

To ensure that the ultrasound device of the present invention is operating safely and effectively, the present invention includes an automatic calibration feature. This feature enables new and replacement treatment heads to be introduced without having to send the entire device away for calibration. The ultrasound device of the present invention automatically determines the complex impedance of the transducer head, after calibration, and maintains acoustic power even in the presence of changes in the real or imaginary portion of the acoustic impedance of the relevant tissue.

DETAILED DESCRIPTION OF THE INVENTION

Figure 1:
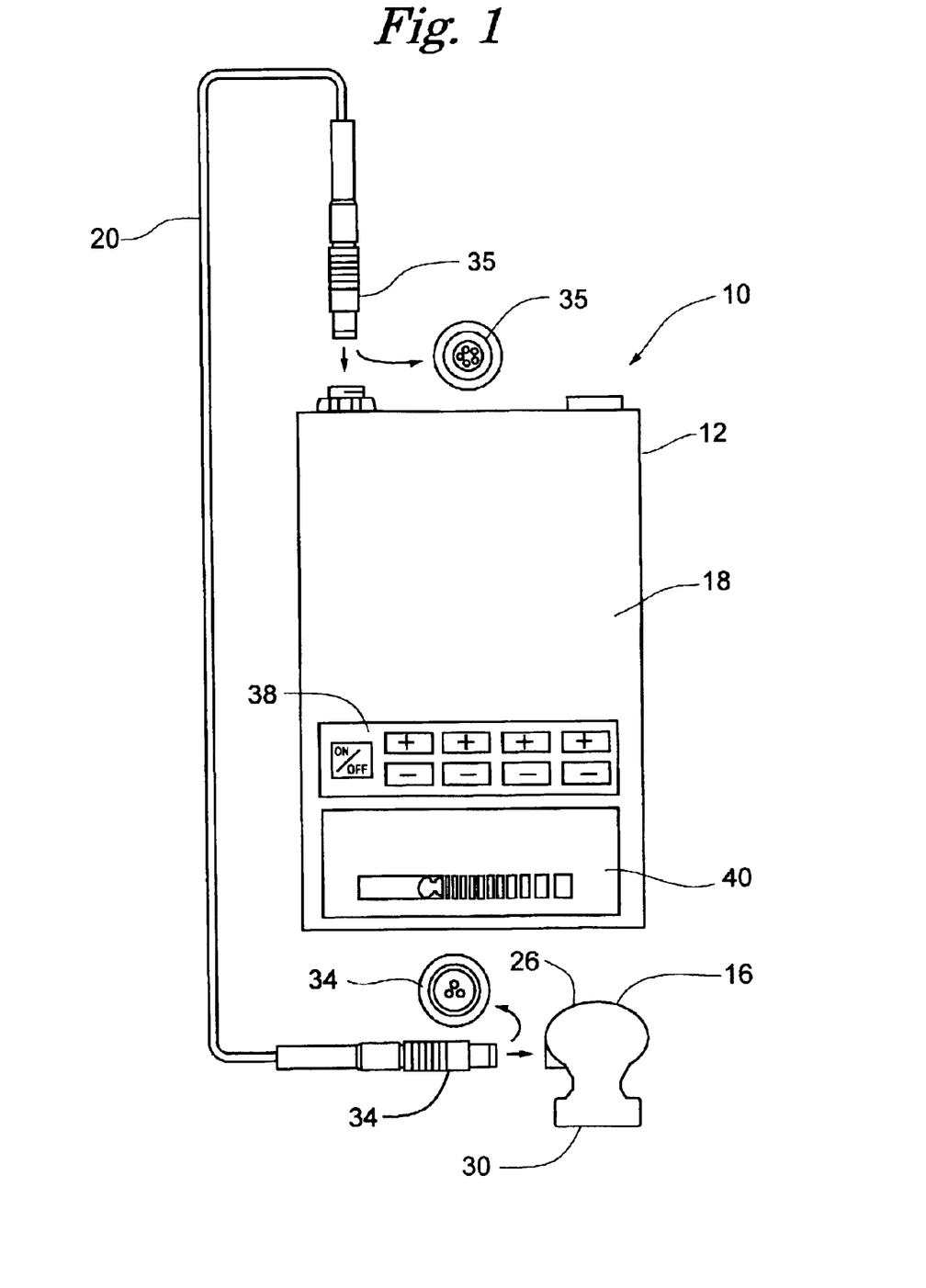
FIG. 1 is a front view of an embodiment of an ultrasound therapeutic device in accordance with the present invention.
Figure 5:
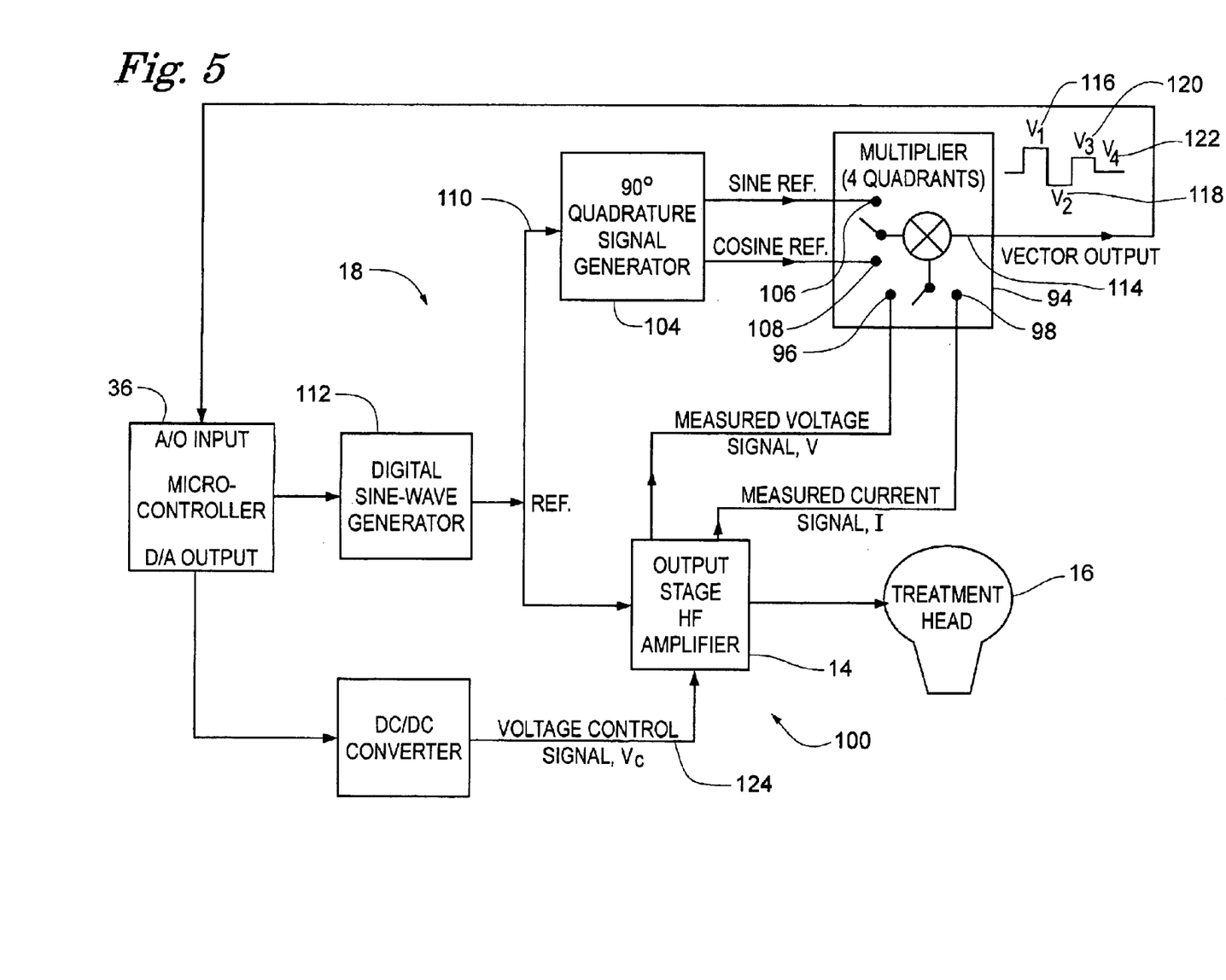
FIG. 5 is a block diagram of the ultrasound system in accordance with an embodiment of the present invention.

Referring primarily to FIGS. 1 and 5, an ultrasound therapeutic system 10 in accordance with the present invention is shown. Specifically, the ultrasound system 10 generally includes a device housing 12, a generator/output stage high frequency amplifier 14, at least one transducer treatment head 16, and a programmable controller 18. The generator 14 and controller 18 are housed within the device housing 12, and are both in operable communication with the transducer 16 via a frequency cable 20.

The generator 14, as shown in FIG. 5, is an electric power source commonly understood by one skilled in the art. For instance, a 48 Volt dc, 0.85 Amp main power source can be utilized in one embodiment, while others could implement similar compatible units. First and second working frequencies of the generator 14 are preferably approximately 1.017 MHz and 3.2 MHz, respectively. It is possible to have a measurable tolerance/deviation of +/−30 KHz on the first frequency and +/−50 KHz on the second frequency. Other output frequencies and permissible frequency tolerances understood to one skilled in the art are also envisioned. The electric power frequency outputs are outputted from the generator 14 to the transducer head 16 through the frequency cable 20.

The at least one transducer treatment head 16 is a transducer head of a predetermined size, with the head 16 generally including a handling portion 26, a transducer element 28, and a treatment surface 30. Each treatment head 16 utilized for the present invention is preferably watertight for optimal use even if completely submerged. Various embodiments can employ different sized treatment heads 16. For instance, ultrasound treatment needs and human body structure and size for a specific focus treatment region on an individual can influence the size of the treatment head. Generally, a large and small head will be interchangeable using the same frequency cable 20. The ultrasonic transducer element 28 of the treatment head 16 is typically constructed of a ceramic (piezo) material. As such, the element 28 will have a maximum output of acoustic power substantially at its resonance frequency. As will be further discussed herein, the treatment head 16 will require initial and, perhaps, periodic self-calibration to guarantee that this optimal resonance frequency for the respective transmission element 28 is obtained and maintained. While various treatment heads 16 can be exchanged to meet specific ultrasonic treatment requirements, there is no need to switch out the cable 20. Conventional devices utilize a unique cable for each treatment head, a practice that can be quite costly, and that can make transportation and storage cumbersome and inconvenient. As discussed herein in describing the cable 20, the present invention eliminates this innate drawback found in conventional devices.

In one embodiment of the present invention, the treatment head 16 further includes a configuration monitoring chip to measure, observe and store data. For instance, operation temperature at the head 16, head 16 serial numbers, head size, calibration data, and a myriad of other information can be stored such that the controller 18 in operable communication with the head 16 can store data to, and retrieve data from, the head 16. This storage and reprogramming can be accomplished with the use of EEPROM, or other non-volatile memory and storage technologies. For instance, a Dallas DS-1820 chip (manufactured and sold by Dallas Semiconductor of Dallas Tex.), or other chips capable of performing these storage and monitoring functions can be utilized without deviating from the spirit and scope of the present invention.

The frequency cable 20 shown in FIG. 1 generally includes at least one set of end connectors 34, and 35 sized and shaped for connecting to respective system 10 components. In particular, at least one end connector 35 can be removably connected to the generator 14 at the housing 12 and the distal end connector 34 of the same cable 20 can be removably connected to the transducer treatment head 16. As such, various treatment heads 16 can be exchanged for operable use with the one common cable 20. This unique swap/exchange feature is possible due to the selectively engageable distal end connector 34. Unlike conventional practice, a fixed and head-specific cable is avoided such that the present invention promotes interchangeability and treatment flexibility, while at the same time promoting storage and transportation. Each of the end connectors 34 and 35 is generally combined or connected to a system component via a socket or plug connection to facilitate maintenance, selective replacement, and adjustable configuration, with each connection preferably being watertight.

Referring primarily to FIGS. 5, the controller 18 includes a microprocessor 36 and control circuitry for providing re-programmable software and hardware control of the present invention. The microprocessor 36 is programmed to receive input and execute control software/algorithms in accordance with predetermined and inputted data. The microprocessor 36 is housed within the housing 12 and is in operable communication with the generator/output stage high frequency amplifier 14, treatment head 16, and each of the other components directly and/or through the controller 18. In various embodiments, flash ROM, EEPROM, non-voltaile memory, and RAM can be employed in conjunction with the microprocessor 36 at the controller 18 for data storage and retrieval.

Referring again to FIG. 1, the housing 12 generally includes a data input portion 38 and a display portion 40. The input portion 38 can comprise input keys or other known input devices for receiving data inputted by an end user in response to prompting from the display portion 40 or from volitional decisions to pursue known treatment goals and program routines. The data input portion 38 and display portion 40 are in operable communication with the controller 18.

In operation, the system 10 of the present invention can prompt the end user to input specific individualized treatment data, wherein the controller 18 can utilize the data to calculate and initiate ultrasound treatment, and provide responsive output and interface adjustments during treatment. In one embodiment, a treatment session or use of the system 10 will involve the following series of inputs, outputs, and automatic adjustments.

First, a treatment "type" must be inputted into the system 10 via prompting on the display portion 40. Generally, there are at least three treatment types: thermal, biological, and phonophoresis. Thermal allows the end user or patient to receive a thermal energy effect from the treatment head 16 at the treatment surface 30. Specifically, such a treatment selection initiates a specific device configuration at the controller 18 wherein the ultrasound energy transmission is converted into thermal energy. Such a conversion leads to a local temperature elevation which particularly effects deeper dense tissue of the patient. As further discussed herein, the proper ultrasound transmission is highly dependent upon inputted histological data from the patient/end user.

The selection of a biological treatment type is directed to a pulsed ultrasound output mode wherein the pulse causes the oscillation of molecules accompanied by marked pressure variations. In turn, this oscillation can lead to the formation of micro-bubbles by cavitation, which in turn can produce a beneficial micro-traumatic stress in indurated tissues, inflammatory foci, local calcified accumulations, and the like.

The selection of a phonophoresis treatment type permits the patient to take advantage of the increased skin permeability that accompanies ultrasound waves. Radiation pressure at the skin due to the inherent permeability increase promotes penetration of medicines through the epidermis layer of the patient. With this treatment selection, there is generally no need for the patient to input histological data or treatment parameters since ideal penetration of the substance is predetermined to facilitate performance and efficiency. In one embodiment, the selection of the phonophoresis treatment mode will cause the microprocessor 36 to set the treatment parameters to the following values: intensity=1.5 W/cm$^2$; duration=8 minutes; frequency=3.2 MHz; emission mode=pulsed; duty cycle=½. Other variations on these values are envisioned and can be employed and pre-programmed into the microprocessor 36 software without deviating from the spirit and scope of the present invention.

In addition, a manual setting is selectable so that the patient can control each of the relevant microprocessor-controlled treatment parameters—intensity, duration, frequency, and emission mode. However, in preferred embodiments, these treatment parameters are calculated and adjusted automatically by the controller 18 implementing software algorithms running on the microprocessor 36.

Specifically, in thermal and biological treatment modes, histological structure data for the individual patient is needed. This histological data generally comprises the target tissue type (tissue to be treated), and the intermediate tissue type and depth (subcutaneous tissue, if any, between the device and the target tissue). Accurate calculation and inputting of this limited histological data will provide the microprocessor 36 with enough information to provide for a highly controlled and efficient treatment of the patient. The necessary treatment parameters and treatment dosage can be selectively and effectively controlled having only this histological data from the patient/user.

The target tissue is generally selected at the input 38 panel of the system 10 from a programmable list. This list can comprise bone, muscle, fat, aponeurosis, tendon, or other targets known to one skilled in the art. In some circumstances, the target tissue will be the only inputted/selected histological data. For instance, if the target tissue is fat, there may not be an intermediate tissue to take into account in controlling the ultrasound treatment to the patient. As such, only the depth of the fat target tissue will need to be inputted.

In other circumstances, the effect of relevant intermediate tissue must be accounted for in determining a treatment dosage. For example, in one operating scenario the target tissue selection may be muscle. As such, it may be necessary to input the thickness or depth of the intermediate tissue between the treatment head 16 and the target muscle tissue. The intermediate tissue depth can be measured with the use of skinfold pinch calipers, estimated on the basis of the physician's or therapist's knowledge of human anatomy (i.e., palpatory anatomy), and the like. The microprocessor 36 can take the inputted histological data alone and determine the proper intensity, duration, frequency, and emission mode. The software will generally select the individual treatment parameters from the following range list: intensity=0 to 2.3 W/cm$^2$; duration 0 to 30 minutes (1800 seconds); frequency=approximately 1 or 3 MHz; emission mode=continuous (1/1) or pulse (½, ¼, or ⅛).

Upon the inputting of user selections and the computed parameter settings and feedback controls, the treatment session will begin by applying the treatment head to the target location on the patient. The treatment head 16 output dosage is controlled by the controller 18. If at any time the head 16 is removed from the patient during the designated treatment period, for a predefined period of time, the controller 18 will initiate a shut down procedure to stop output from the generator 14 to the treatment head 16.

Thermal Treatment Mode

In thermal mode, the algorithmic simulation functions of the microprocessor 36 automatically calculate and control the treatment dosage to create a tissue temperature elevation based on the relevant histological data. Preferably, the intensity and duration parameters are fully correlated. A change, either manually or automatically, will cause the microprocessor 36 software to automatically change the remaining value correspondingly such that the product of the at least two values remains substantially unchanged. The product of intensity and duration is generally used to produce a target tissue temperature elevation of 7 degrees Celsius. A continuous transmission (1/1), rather than pulsed, is typically initiated by the software in thermal mode since such a transmission promotes the desired tissue temperature elevation.

Figure 2A:
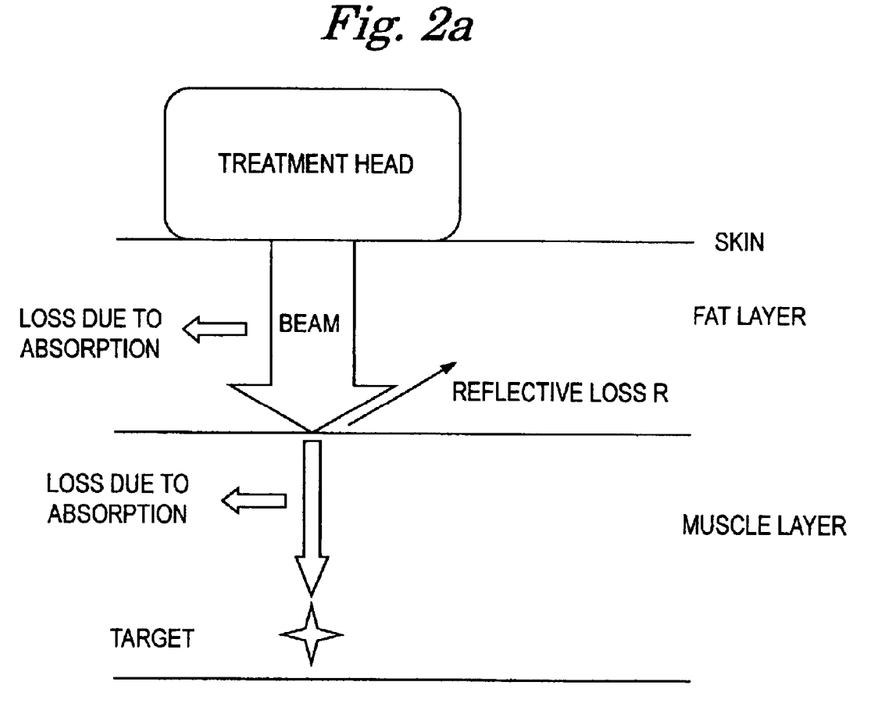
FIG. 2a is a diagram demonstrating ultrasonic beam absorption and reflection losses resulting from a specific human tissue structure.

This product of acoustic intensity and treatment duration is the treatment dosage. As shown in FIG. 2a, the dosage is a function of the losses from absorption of the ultrasound beam as it travels through relevant tissues and the losses from reflections at the interfaces between adjacent tissues having different acoustic impedances. The quantity of ultrasound which ultimately reaches the target tissue is the therapeutically effective energy which participates in the local elevation of tissue temperature. Since the temperature elevation depends on dosage, the user can change the remaining treatment duration or the intensity at anytime.

The software selects the frequency of the output signal based on the histological data inputted. Specifically, the target depth and intermediate tissue dictate the level of penetration required to provide an effective therapeutic dose. In one embodiment, a frequency of approximately 1 MHz is utilized to penetrate relatively deep tissue since such a signal will be less absorbed by the tissue. Conversely, a frequency of approximately 3 MHz is utilized to penetrate relatively shallow tissue. Preferably, the microprocessor 36 software performs simulations at both the 1 MHz and 3 MHz levels to determine which signal will require the smallest dosage while still obtaining the requisite therapeutic effect. Other predetermined or variable frequency determinations can be made as well without deviating from the spirit and scope of the present invention.

Figure 2B:
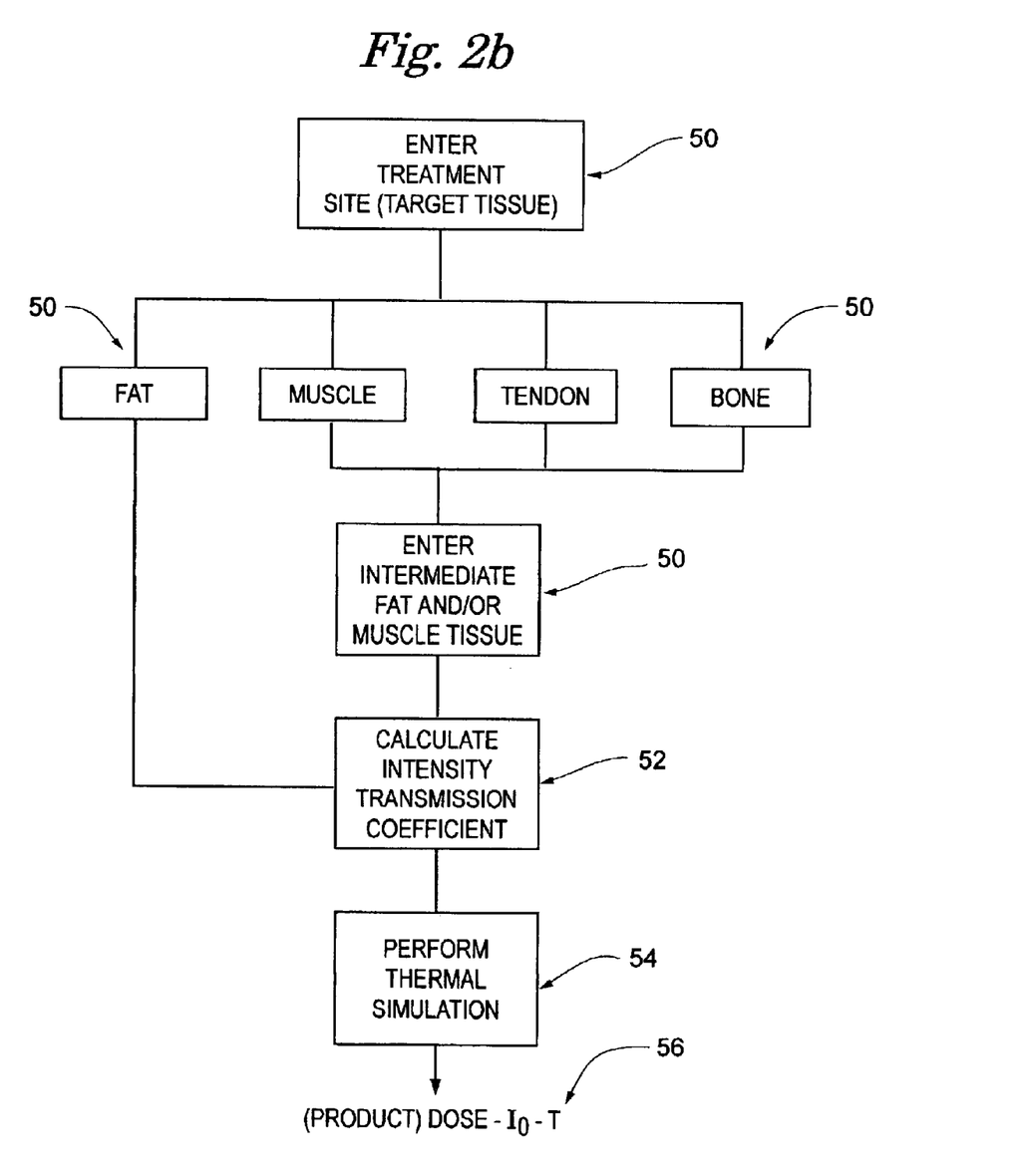
FIG. 2b is a block diagram of the operation of thermal dosage control in accordance with an embodiment of the present invention.

Referring to FIG. 2b, one embodiment of the automatic mode dosage determination software is shown. First, the user is required to enter specific data at an initial input stage 50. At this data input stage 50, the user is first prompted to enter a target tissue type. Generally, fat, muscle, tendon, and bone are the tissue types available for selection or input. Once the tissue selection has been made, the user is prompted to input the depth of the tissue between the target and the treatment head 16. It is preferred that this depth be entered in centimeters, but other measurements are also envisioned. For instance, if the target tissue inputted is tendon, it is possible that there is muscle and/or fat intermediate the tendon. As discussed, this tissue intermediate the target tissue must be considered before calculating a truly effective treatment dosage. Tissue depth and thickness calculations can be performed using techniques known to one skilled in the art. For instance, pinch calipers and the physician's or therapist's knowledge of the human anatomy can be employed. Depending on the presence of intermediate fat or muscle, and the corresponding depth for the intermediate tissue, the microprocessor 36 software will process the data at an intensity transmission stage 52.

At the intensity transmission stage 52, the actual transmission effects of the tissue layer structure are considered in calculating a transmission coefficient $\tau$. Variable $\tau$ represents reflection losses caused as a result of the layers and tissue interfaces to assist in providing for needed adjustment in the dosage, wherein $\tau$ is represented in equation form as:

$$\tau = 1 - R_{ij}$$

where $R_{ij}$ is the tissue intensity reflection coefficient between layer i and j. This reflection coefficient-depends on the acoustic impedance of layer i ($Z_i$) and layer j ($Z_j$):

$$R_{ij} = \frac{(z_i - z_j)^2}{(z_i + z_j)^2}$$

Defined tissue impedance levels for bone, skin, tendon, muscle, and fat are known and processed depending on the referenced tissue inputs such that each impedance value corresponds to a wave reflection at the interface of adjacent tissues. For instance, a $\tau$ value representing the influence of the reflection characteristics of interfacing fat and tendon tissue ($\tau_{ft}$) will equate to a coefficient of 0.934, which represents a 93.4% transmission intensity and a 6.6% loss due to reflections at the interface. Assuming m=muscle, t=tendon, f=fat, and b=bone, other possible transmission loss characteristics can be accounted for as $\tau_{mt}$=0.974, $\tau_{st}$=0.968, $\tau_{sb}$=0.748, $\tau_{fb}$=0.685, $\tau_{mb}$=0.761, $\tau_{fm}$=0.990, $\tau_{fs}$=0.990, $\tau_{sm}$=0.890, $\tau_{tb}$=0.870, and other transmission coefficients known to one skilled in the art.

Additionally, reduction of the available energy at the target tissue is caused by a beam attenuation (a) phenomenon. First, this attenuation is due to absorption ($\alpha$), which is a transformation of a fraction of the acoustic beam into heat. Second, beam diffusion or scattering (d) also contributes to the beam attenuation. As such, a=$\alpha$+d. For scenarios involving soft tissues and at frequencies in the MHz range, scattering may be neglected so that a=$\alpha$, for a unit measurement of Np/cm$^2$ (Nepers per square centimeters).

At the thermal simulation stage 54, the appropriate ultrasound frequency intensity ($I_O$) and treatment duration (T) are calculated such that the product of the intensity and the treatment duration equals the treatment radiation dosage D. In obtaining the correct variables for this dosage formula, an ideal frequency must be calculated. This ideal frequency for the ultrasound intensity $I_0$ is based on a simulation run for at least two frequencies—1 MHz and 3 MHz. It should be noted that these frequencies, while preferred, are not in any way exhaustive in nature. For instance, other frequency ranges and values can be utilized depending on the particular desired therapeutic effect. In addition, values such as 1 MHz and 3 MHz are obviously rounded for ease of explanation and calculation. In one embodiment, the frequency intensities can be assigned as 1.017 MHz±30 KHz, and 3.2 MHz±50 KHz. Other values and corresponding ranges are also envisioned.

In an embodiment performing an individual simulation run for both 1 MHz and 3 MHz levels, the following equation is implemented:

$$D = (I_0 \, t) = \frac{TC_v e^{2f(a1e1+a2e2+a3e3)}}{2\alpha f \tau}$$

wherein the frequency value $f$ is inserted by the microprocessor 36 program as either 1 or 3 depending on the particular simulation run, T is the treatment duration (i.e., seconds), $C_v$ is a thermal coefficient (heat capacity per unit volume), a is the attenuation coefficient, and $\tau$ again represents consideration of the effects of the actual tissue layer structure in an intensity transmission coefficient. As the appropriate $\tau$ value has already been processed in the intensity transmission stage 52, that value is automatically inserted to promote evaluation of true tissue effects during the treatment simulation. The attenuation coefficient a represents absorption within the tissue layer of a level of energy lost in the form of heat. Variable attenuation coefficient values known to one skilled in the art as being representative of these tissue-specific heat absorption effects can be employed without deviating from the spirit and scope of the present invention.

With calculation and insertion of the appropriate values into the simulation equation, a product A is assigned the resulting dosage product for 1 MHz, and B is assigned the dosage product for 3 MHz. The products A and B are compared and analyzed to determine the smallest dose D that can be employed while still reaching the desired therapeutic effect based on known histological data from the user. Preferably, if A B then a value of 3 MHz is assigned as the output frequency, else a value of 1 MHz is assigned. Next, intensity and treatment duration end points are examined based on the simulation results to determine optimum values for generating the product dosage, wherein the resulting product dosage is processed to determine whether it falls within an acceptable range defined by predetermined minimum and maximum product dosage values. These values, in one embodiment, can be a minimum dosage value of 6 Ws/cm$^2$ (Watt seconds per square centimeter) and a maximum value of 5400 Ws/cm². For instance, if a maximum product dosage of 5400 is calculated based on the above simulation equations, then a set intensity $I_0$ is assigned to approximately 3 W/cm², with a corresponding treatment duration of approximately 1800 seconds. Further, the microprocessor 36 can downsize the dosage if it exceeds the maximum, up the dosage if it equates to a value below the acceptable minimum level, and can process variable levels between these end point values. At the completion of the comparison and simulation, the duration T, and intensity $I_0$ are known values that can be linked at a product dosage stage 56, wherein the product dosage $P = I_0 \cdot T$. This equation links the variables such that a change in one variable can cause the microprocessor 36 program to correspondingly change the other variables to produce a constant dosage.

Biological Treatment Mode

In biological mode, the algorithmic simulation functions of the microprocessor 36 take tissue configuration into account and automatically select the treatment parameters that will produce the required mechanical effect and minimize tissue temperature elevation. Whereas a tissue temperature elevation is the desired effect in the thermal treatment mode, a thermal effect is not beneficial and must be minimized in biological mode in favor of a mechanical effect.

The software automatically determines the intensity, frequency, emission mode and duration of treatment needed in biological mode. In one embodiment, these values are obtained from a look-up table. The desired mechanical effects of biological mode are typically induced using a pulsed emission mode with different duty cycles. The ultrasonic pressure waves produce an oscillation of molecules in the target tissue. This oscillation creates microscopic bubbles called cavitation bubbles that generate small shockwaves in the tissue when they collapse. These small shockwaves induce microscopic mechanical effects in the tissues that enhance the healing process by causing the tissues to grow stronger in reaction to the micro-traumatic stress effect. Biological mode is typically beneficial to indurated tissues, inflamed areas, local calcifications, accumulations of blood such as hematomas, bruises and blood clots, and areas of fibrosis.

Phonophoresis Treatment Mode

In phonophoresis mode, ultrasound is employed to aid in the penetration of drugs through the skin and into target tissue. Phonophroesis mode enhances local application of a drug by increasing the permeability of the skin and exerting a radiation pressure that promotes the penetration of drugs deep into tissues.

In one embodiment, all software parameters in phonophoresis mode are fixed and the dose is held constant. While the intensity and treatment duration may be adjusted, the microprocessor 36 software links the two conditions inversely such that an increase inputted in either will cause the software to decrease the other. Again, phonophoresis treatment mode will generally cause the microprocessor 36 to set the treatment parameters to the following values: intensity=1.5 W/cm²; duration=8 minutes (480 seconds); frequency=3.2 MHz; emission mode=pulsed; duty cycle=½.

Automatic Feedback Loop

Ultrasound treatment is more effective when constant acoustic power is delivered to the tissue. The ultrasound generator 14 includes a novel feedback loop feature that operates to maintain the delivery of acoustic power at a constant level. A simplified block diagram 100 of the feedback loop in accordance with the present invention is shown in FIG. 5.

The feedback loop operates to measure a coupling efficiency between the transducer treatment head 16 and the biological tissue of the patient. The coupling efficiency is a ratio of the acoustic power effectively transmitted into the patient to the electric power delivered to the transducer treatment head 16 from the generator 14. Thus, the coupling efficiency can be expressed as:

$$\eta = \frac{P_a}{P_e}$$

where $\eta$ is the coupling efficiency, $P_a$ is the effective transmitted acoustic power and $P_e$ is the delivered electric power. The coupling efficiency is dependent on patient tissue configuration as tissue impedance varies with tissue type. For example, if the tissue in contact with the transducer treatment head 16 is soft, i.e., skin with a thick layer of fat, the acoustic impedance will be low and the coupling efficiency will be low. If the tissue is instead skin with a thin layer of fat and a large bone near the skin surface, the coupling efficiency will be higher.

The microprocessor 36 adjusts the electric power, $P_e$, such that the effective acoustic power transmitted to the patient is maintained constant regardless of the tissue type encountered. While the coupling efficiency, $\eta$, can be expressed by the above equation, the microprocessor 36 uses a modified equation to calculate $\eta$ and determine the transducer efficiency for the purpose of adjusting the electric power to maintain the acoustic power.

Figure 4A:
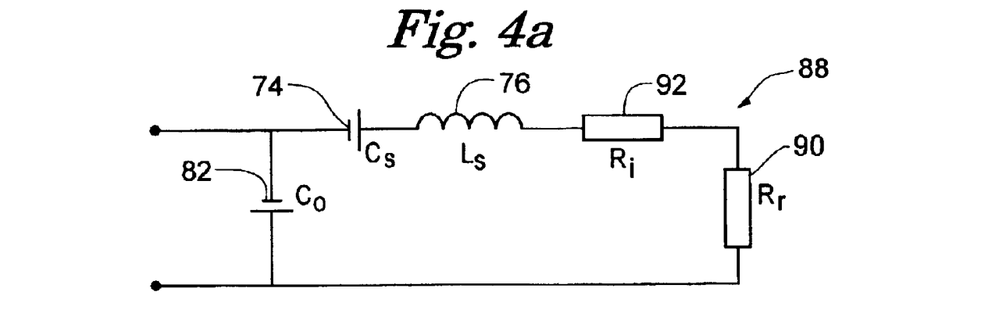
FIG. 4a is a diagram of transducer circuitry in accordance with an embodiment of the present invention.
Figure 4B:
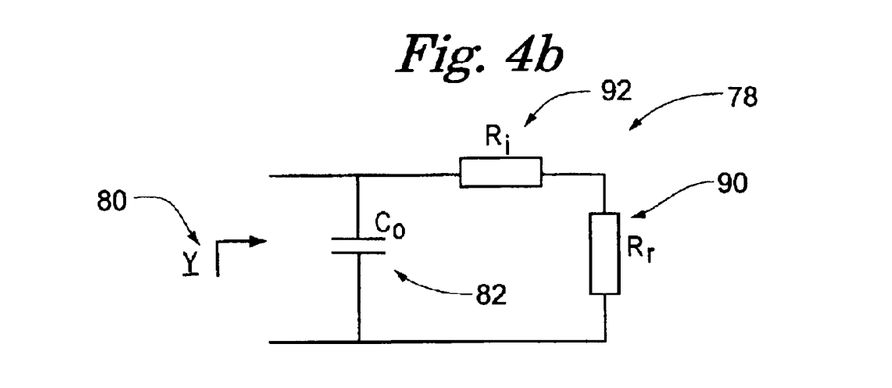
FIG. 4b is a diagram of transducer circuitry in accordance with an embodiment of the present invention.

FIG. 4a depicts an equivalent circuit 88 of the piezo transducer close to its resonant frequency in accordance with the present invention. In the equivalent circuit 88, internal mechanical losses are represented by $R_i$ 92, and $R_r$ 90 represents the radiation resistance. The acoustic power emitted can be viewed as the power dissipated across the radiation resistance, $R_r$ 90. Where $R_s$ represents the sum of $R_i$ 92 and $R_r$ 90, the value of $R_s$ can be obtained by measuring the overall admittance (the reciprocal of the overall impedance) of the equivalent circuit at resonant frequency. At resonant frequency, $C_s$ 74 and $L_s$ 76 resonate together and further reduce the equivalent circuit 88 to the circuit 78 depicted in FIG. 4b. The overall (complex) admittance, $\underline{Y}$ 80, of the circuit 78 (and the equivalent circuit 88 of FIG. 4a) is the sum of the admittance of the resistance $R_s$ (where $R_s = R_r + R_i$) and the admittance of the capacitor $C_0$ 82, such that:

$$\underline{Y} = Y_R + Y_C = G + jB = \frac{1}{R_s} + \frac{1}{j\omega C_0}$$

where G, the conductance, is the real portion of the admittance and B, the susceptance, is the imaginary portion. Thus, the conductance, G, of the equivalent circuit 88 of the transducer at resonant frequency is $1/R_s$, which results in the value of $R_s$ itself.

Figure 3:
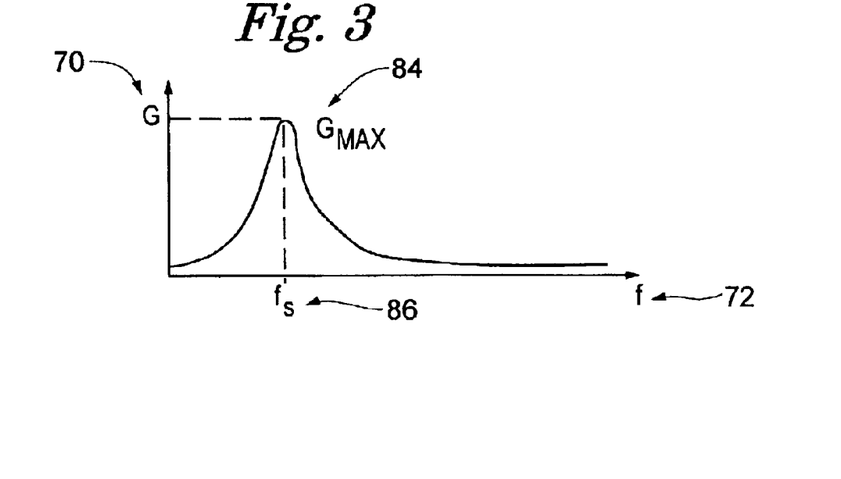
FIG. 3 is a diagram plotting the frequency versus conductance of a transducer in accordance with an embodiment of the present invention.

FIG. 3 is a diagram plotting the frequency 72 versus conductance 70 of a transducer 16 in accordance with the present invention. To measure the value of $R_s$, it is necessary to find the maximum value of the real portion of the admittance, $G_{max}$ 84, where $$G_{max} = \frac{1}{R_s}$$

This will also provide the series resonant frequency, $f_s$ 86. The equation for $\underline{Y}$ 80, above holds true only at the resonant frequency $f_s$ 86, of the piezo transducer 16, defined by the maximum of the real portion of $\underline{Y}$ 80, $G_{max}$ 84. FIG. 4 depicts the shape of a curve of the conductance, G 70, plotted against frequency, f 72, and demonstrates the relationship between $G_{max}$ 84 and $f_s$ 86. Note that the series resonant frequency $f_s$ 86 will vary for each transducer treatment head 16 used. Calibration of a particular transducer treatment head 16 consists of the microprocessor scanning the frequency of the signal and simultaneously monitoring the conductance, G 70, in order to detect a maximum (see FIG. 3). The locus of the maximum, $G_{max}$ 84, defines the resonant frequency, $f_s$ 86. This calibration procedure is initiated by a user while the transducer 16 is unloaded (e.g., not in contact with any tissue) and is discussed in greater detail in the following section.

Referring again to FIGS. 4a and 4b, the effective radiation resistance $R_r$ 90 actually represents the transmission of ultrasonic energy out of the transducer. When measuring the transducer radiating into a tissue load, the maximum conductance, $G_{max}$ 84 of FIG. 3 as discussed above, actually provides:

$$G_{\max} = G_{tissue} = \frac{1}{R_{tissue} + R_i}$$

When the maximum admittance is measured without any load, the maximum conductance, $G_{max}$ 84 (the real portion of the admittance), is almost exclusively the internal losses:

$$G_{\max} = G_0 = \frac{1}{R_i}$$

where $G_0$ is the series conductance of the unloaded transducer treatment head 16. Thus, if the dielectric losses are neglected, the transducer 16 efficiency can be approximated by:

$$\eta_{ea} = \frac{G_0 - G_{tissue}}{G_0}$$

Figure 6:
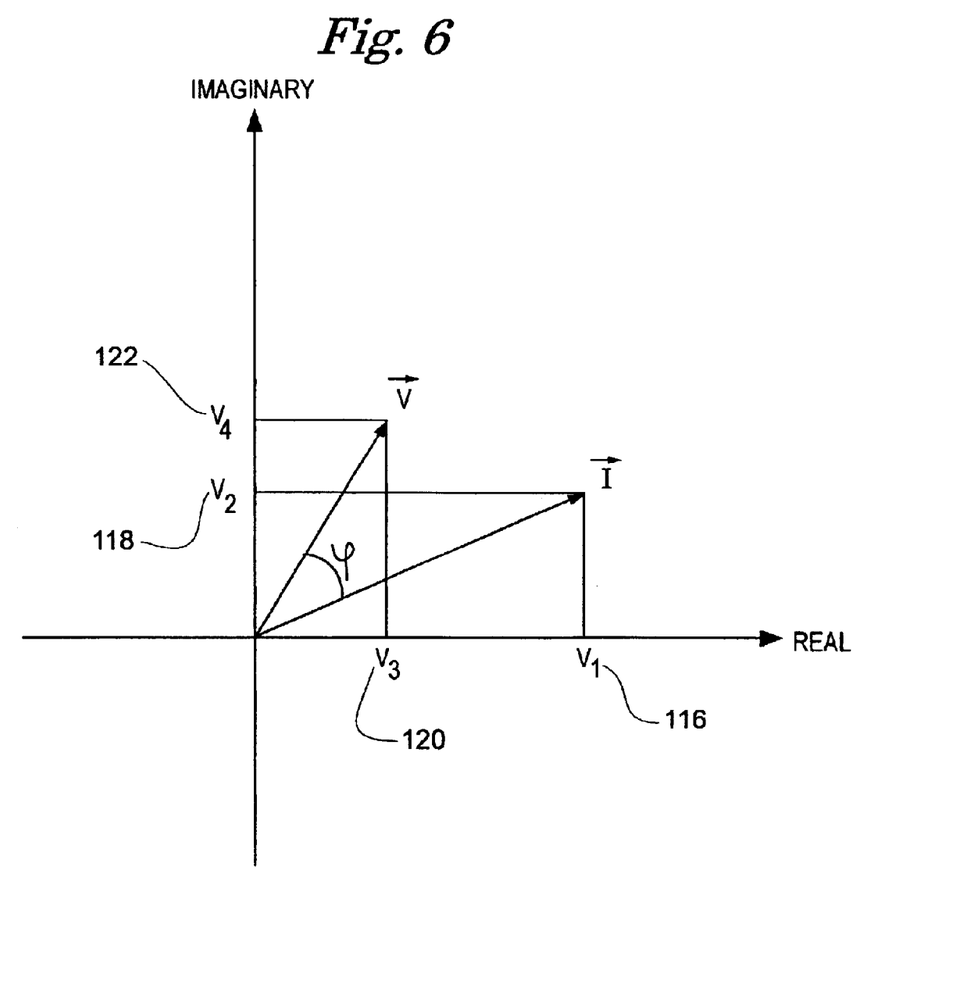
FIG. 6 is a diagram depicting the real and imaginary components of measured voltage and current in accordance with an embodiment of the present invention.

FIG. 5 represents a block diagram of the ultrasound system in accordance with an embodiment of the present invention. In operation, the analog multiplier 94 receives a measured voltage signal 96 and a measured current signal 98 from the generator/output stage high frequency amplifier 14. The analog multiplier 94 is also connected to a 90-degree quadrature signal generator 104. The 90-degree quadrature signal generator 104 receives a reference sine wave 110 from the digital sine wave generator 112 and in turn provides the analog multiplier 94 with sine 106 and cosine 108 reference signals. Vector voltage $V_i$ 114, the output of the analog multiplier 94, represents $V_1$ 116, $V_2$ 118, $V_3$ 120 and $V_4$ 122, which are generated by switching the inputs of the analog multiplier 94 circuit as shown in FIG. 6.

The electrical power $P_e$ can then be calculated from $V_i$ 114, where:

$$P_e = |V^{\omega}| \cdot |I^{\omega}| \cos\varphi$$

The complex transducer 16 impedance $\underline{Z}$ can be calculated by dividing $\underline{V}$ by $\underline{I}$, and the conductance G is the real portion of the inverse of $\underline{Z}$, or the real portion of $\underline{I}$ over $\underline{V}$. After the efficiency η and the electric power $P_e$ are calculated from the input voltage, the effective transmitted acoustic power $P_a$ can be calculated. The voltage control signal $V_c$ 124 can then be adjusted and readjusted accordingly to maintain the delivery of acoustic power at a constant level.

In sum, the procedure used by the microprocessor 36 for determining the efficiency of the transducer is as follows: (1) determine vector voltage $V_i$ 114, having components $V_1$ 116, $V_2$ 118, $V_3$ 120 and $V_4$ 122, by measurement; (2) calculate the coupling efficiency and the electric power from the vector voltage 114; (3) calculate the effective transmitted acoustic power; and (4) readjust the voltage control signal 124 accordingly. In operation, the microprocessor 36 is thus able to maintain a constant level of effective acoustic power transmitted to the patient by adjusting the electric power approximately every 20 milliseconds in response to the coupling efficiency calculated in the feedback loop. Additionally, during emission, the microprocessor 36 regularly scans the $G_{max}$ 84 value in order to detect if $f_s$ 86 has shifted and readjusts accordingly.

Further, during transmission the microprocessor 36 monitors the feedback loop, with notification provided if the feedback loop fails. A failure of the feedback loop may occur, for example, when the user removes the treatment head 16 from the patient, which results in insufficient acoustic coupling. In the event of such a failure, transmission is stopped and the ultrasound therapeutic system 10 puts itself into resonance search and output calculation mode. Once the acoustic coupling returns to an acceptable level (by the user having placed the treatment head 16 back in contact with a patient's skin), the feedback loop is restarted and normal operation resumes. The microprocessor 36 also monitors the resonant frequency 86 search and centering, and the presence of the treatment head 16. Throughout, the system 10 continuously scans the frequency over a range around the nominal resonant frequency $f_s$ 86 to ensure that the frequency of the excitation signal remains centered on the maximum conductance $G_{max}$ 84.

Automatic Calibration

For safe and effective ultrasound treatment, properly calibrated equipment is required. The ultrasound therapeutic system 10 in accordance with the present invention generally includes a calibration procedure that enables a user to calibrate the transducer treatment heads 16 whenever necessary without having to send the entire ultrasound therapeutic system 10 back to the factory. In addition, the calibration procedure enables the user to calibrate an entirely new transducer treatment head 16 as soon as it is received, facilitating easy and efficient replacement of worn or dysfunctional parts.

The calibration procedure of the present invention automatically determines the impedance of the transducer treatment heads 16. The procedure is based upon the measurement of the series conductance $G_0$ of the transducer treatment head when it is unloaded. The series conductance is the real portion of the admittance and the reciprocal of the impedance and represents the losses of the transducer treatment head 16 itself. Referring primarily to FIG. 5, the microprocessor 36 calibration software scans the generator frequency to determine the maximum value of $G_0$ that also yields the resonant frequency $f_s$ 86 of the transducer treatment head 16. The measurement of $G_0$ is done by a demodulation method in which the current 98 and voltage signals 96 from the treatment head are multiplied by quadrature reference signals 106 and 108. This method considers the com plex impedance and thus accounts for the corresponding phase shifts between current and voltage ($\theta$):

$$Z = \frac{V}{I} = Ze^{-j\theta}$$

where $\theta$ is the phase of the complex impedance. The complex admittance $\underline{Y}$ can then be determined, the real part of which is the series conductance $G_0$:

$$G_0 = Re\{Y\} = (R^{-1})$$

where $R = R_s = R_i$ as $R_r = 0$ with no acoustic loading (see FIGS. 4a and 4b). During the emission of ultrasound energy into a patient's tissue, the ultrasound therapeutic system 10 constantly measures the maximum series conductance under load, $G_{tissue}$, using the same method:

$$G_{tissue} = \frac{1}{R_s} = \frac{1}{R_r + R_i}$$

The system 10 then determines the real-time electro-acoustic coupling efficiency $\eta$:

$$\eta = \frac{G_0 - G_{tissue}}{G_0}$$

In operation, the user initiates the calibration procedure. Ideally the procedure is run annually, but other periodic calibrations are envisioned as well. With the transducer 16 unloaded, the microprocessor 36 scans the excitation frequency in a predefined range around the resonant frequency 86 and looks for the maximum conductance $G_0$. $G_0$ is representative of the transducer 16 losses as it is the real portion of the impedance when no acoustic energy is produced by the piezo transducer 16. The microprocessor 36 records the value of $G_0$ and the resonant frequency 86 for later use.

During normal use, the electro-acoustic coupling efficiency $\eta$ is calculated from the actual loaded conductance $G_{tissue}$, where $G_{max} = G_{tissue}$, and from the recorded value of $G_0$ adjusted according to the equation above. In one embodiment, this calibration procedure allows the system 10 to compensate for any changes in the electrical characteristics of the transducer 16, including the acoustic load, changes in the capacitance $C_0$ due to aging, temperature driven changes, and like characteristics.

In this automatic calibration procedure, the system 10 considers both impedance amplitude and phase, allowing for consideration of complex changes. Thus, the power transmitted to the tissue remains accurate despite shifts in the resonant frequency 86 due to slight imaginary components in the acoustic impedance of the target tissues being treated.

Those skilled in the art will appreciate that other embodiments in addition to the ones described herein are indicated to be within the scope and breadth of the present application. Accordingly, the applicant intends to be limited only by the claims appended hereto.

What is claimed is:

1. An ultrasound system for physical therapy comprising:
a generator for generating an ultrasound output signal;
at least one ultrasonic transducer capable of receiving the ultrasound output signal to generate an acoustic treatment wave;
an input device for receiving histological tissue data from a user including target treatment tissue type, and intermediate tissue structure; and
a controller including treatment software wherein the inputted histological tissue data is processed through at least a treatment simulation to calculate an ultrasound dosage including an acoustic intensity value and a treatment duration value, wherein the target tissue type and the acoustic treatment wave effects of the inputted intermediate tissue structure are processed to generate the acoustic intensity value and the treatment duration value.

2. The system of claim 1, wherein the controller, at the thermal simulation, processes at least two output frequency values to determine the correct treatment duration and acoustic intensity values for the ultrasound dosage.

3. The system of claim 1, wherein the at least two output frequency values processed at the simulation stage are a first frequency of approximately 1 MHz and a second frequency of approximately 3 MHz for calculating the ultrasound dosage, the controller analyzing use of each first and second frequencies to select the preferred output frequency resulting in the smallest ultrasound dosage that can be employed based on the inputted histological tissue data.

4. The system of claim 3, wherein the treatment software links the treatment duration value and the acoustic intensity value such that a change in one results in a proportional change in the other to maintain a constant ultrasound dosage.

5. The system of claim 3, wherein the controller further processes the selected ultrasound dosage following the thermal simulation to ensure that the treatment intensity value and the treatment duration value are within acceptable limits.

6. The system of claim 1, wherein the input device is further capable of receiving a treatment mode selection.

7. The system of claim 6, wherein the treatment mode selections are from a group consisting of: thermal, biological, and phonophoresis modes.

8. The system of claim 1, wherein the controller processes the inputted histological tissue data to compute a treatment intensity coefficient that represents the acoustic energy losses caused by the intermediate tissue structure, with the treatment intensity coefficient being used in the thermal simulation.

9. The system of claim 8, wherein the controller calculates the acoustic energy losses to account for the change in acoustic impedance caused by the reflection of the treatment wave at tissue interfaces.

10. The system of claim 8, wherein the controller calculates the acoustic energy losses to account for the absorption of energy in the tissue from heat generated therein.

11. The system of claim 1, further including at least one cable adapted to communicate the output signal from the generator to the transducer, the cable having an interchangeable head connector end capable of selectively receiving a plurality of treatment heads.

12. The system of claim 11, wherein the interchangeable head connector end of the at least one cable is capable of receiving treatment heads having different acoustic treatment wave capabilities.

13. An ultrasound system for physical therapy comprising:
generating means for generating an ultrasound output signal;
delivery means for receiving the ultrasound output signal to deliver an acoustic treatment wave;
inputting means for receiving histological tissue data from a user including target treatment tissue type, and intermediate tissue structure; and
control means for running treatment software, wherein the inputted histological tissue data is processed through at least a treatment simulation to calculate an ultrasound dosage including an acoustic intensity value and a treatment duration value, wherein the target tissue type and the acoustic treatment wave effects of the inputted intermediate tissue structure are processed to generate the acoustic intensity value and the treatment duration value.

14. The system of claim 13, wherein the treatment software links the treatment duration value and the acoustic intensity value such that a change in one results in a proportional change in the other to maintain a constant ultrasound dosage.

15. An ultrasound system for physical therapy comprising:
   a generator unit for generating an output signal;
   at least one ultrasonic transducer capable of receiving the output signal to generate acoustic output;
   an input device for receiving a treatment mode selection and histological tissue data from a user, the treatment mode being selectable from biological, thermal, and phonophoresis modes; and
   a controller programmed to calculate an ultrasound dosage after processing the inputted mode selection and histological tissue data, wherein the ultrasound dosage includes a treatment duration value and an acoustic intensity value.

16. The system of claim 15, wherein the phonophoresis treatment mode selection causes the controller to automatically select predefined treatment duration and acoustic intensity values.

17. The system of claim 16, wherein the predefined treatment intensity value is approximately 1.5 W/cm$^2$.

18. The system of claim 16, wherein the predefined treatment duration value is approximately 8 minutes.

19. The system of claim 15, wherein the selection of the phonophoresis treatment mode causes the controller to automatically select a predefined output frequency of approximately 3 MHz.

20. The system of claim 15, wherein the selection of the thermal treatment mode causes the controller to process the ultrasound dosage through at least program thermal simulation stage.

21. The system of claim 20, wherein the controller, at the thermal simulation stage, processes at least two output frequency values to determine the correct treatment duration and acoustic intensity values for the ultrasound dosage.

22. The system of claim 21, wherein the at least two output frequency values processed at the simulation stage are a first frequency of approximately 1 MHz and a second frequency of approximately 3 MHz, with the controller analyzing use of each first and second frequencies to determine the preferred output frequency resulting in the smallest ultrasound dosage that can be employed based on the inputted histological tissue data.

23. An ultrasound system for physical therapy comprising:
   generating means for generating an ultrasound output;
   delivery means for receiving the ultrasound output to generate acoustic output;
   inputting means for receiving a treatment mode selection and histological tissue data, the treatment mode being selectable from biological, thermal, and phonophoresis modes; and
   control means for running treatment software, including calculating an ultrasound dosage after analyzing the inputted mode selection and the histological tissue data.

24. A method of therapy with an ultrasound system having a transducer treatment head for applying acoustic waves to a user, comprising the steps of:
   determining tissue depth data for a user;
   inputting into the ultrasound system histological tissue data, including
      inputting target tissue data;
      inputting tissue type data, and tissue depth data for tissue intermediate the treatment head and the target tissue; and
   processing the histological tissue data at a controller of the ultrasound system wherein the controller includes a simulation algorithm to process the inputted histological tissue data to calculate a treatment dose including a treatment duration value, and an acoustic intensity value.

25. The method of claim 24, wherein two output frequency values are processed during the simulation algorithm to determine the correct treatment duration and acoustic intensity values for the treatment dose.

26. The method of claim 25, wherein the two output frequency values processed are a first frequency value of approximately 1 MHz and a second frequency value of approximately 3 MHz.

27. The method of claim 26, wherein each of the first and second frequency values are individually processed through the simulation algorithm to determine the smallest treatment dose that can be employed in light of the known histological tissue data.

28. The method of claim 24, wherein the product of the treatment duration value and the acoustic intensity value equals the treatment dose, with the two values of the treatment dose being linked such that a change in one provides a proportional change in the other to maintain a constant treatment dose.

29. A method of ultrasonic therapeutic treatment comprising the steps of:
   selecting at an ultrasonic therapy device a treatment mode from options of biological, thermal, and phonophoresis mode;
   inputting into the input device histological tissue data for a user and
   processing at a controller the inputted treatment mode selection and the histological tissue data to calculate an output treatment dosage including a treatment duration value and an acoustic intensity value for communication to a transducer treatment head.

30. The method of claim 29, wherein the output treatment dosage processed at the controller includes a axed treatment duration value and a fixed treatment intensity value when a user selects phonophoresis as the treatment mode option.

31. The method of claim 30, wherein the fixed treatment intensity value is approximately 1.5 W/cm$^2$.

32. The method of claim 30, wherein the fixed treatment duration value is approximately 8 minutes.

33. The method of claim 29, wherein input selection of the phonophoresis treatment mode causes the controller to automatically select a fixed output frequency of approximately 3 MHz.

34. The method of claim 29, wherein inputting the histological tissue data after selecting the thermal treatment mode option includes inputting target tissue data and inputting tissue structure data for tissue intermediate the target tissue and the transducer bead.

35. The method of claim 34, wherein selecting the thermal treatment mode selection further causes the controller to perform at least a thermal simulation to calculate the output treatment dosage.

36. The method of claim 35, wherein, at the thermal simulation, the controller performs the steps of processing at least two output frequency values to determine the correct treatment duration and acoustic intensity values for the output treatment dosage.

37. The method of claim 36, wherein the step of processing at least two output frequency values includes processing a first frequency of approximately 1 MHz and a second frequency of approximately 3 MHz with the controller analyzing use of each first and second frequencies to determine the preferred output frequency resulting in the smallest output treatment dosage that can be employed based on the inputted histological tissue data.

* * * * *